(12) United States Patent
Shinoda

(10) Patent No.: US 8,203,711 B2
(45) Date of Patent: Jun. 19, 2012

(54) LIGHT IRRADIATION METHOD, LIGHT IRRADIATION DEVICE, AND FINE PARTICLE ANALYZING APPARATUS

(75) Inventor: Masataka Shinoda, Tokyo (JP)

(73) Assignee: Sony Corporation, Tokyo (JP)

( * ) Notice: Subject to any disclaimer, the term of this patent is extended or adjusted under 35 U.S.C. 154(b) by 256 days.

(21) Appl. No.: 12/185,627

(22) Filed: Aug. 4, 2008

(65) Prior Publication Data

US 2009/0059223 A1    Mar. 5, 2009

(30) Foreign Application Priority Data

Sep. 4, 2007    (JP) ................................. 2007-228932

(51) Int. Cl.
*G01N 21/00*    (2006.01)
(52) U.S. Cl. ...................................................... 356/337
(58) Field of Classification Search ................... 356/337
See application file for complete search history.

(56) References Cited

U.S. PATENT DOCUMENTS

| | | | |
|---|---|---|---|
| 4,786,165 A * | 11/1988 | Yamamoto et al. ............. 356/23 |
| 4,885,473 A | 12/1989 | Shofner et al. | |
| 4,906,094 A * | 3/1990 | Ashida ........................... 356/336 |
| 4,920,275 A | 4/1990 | Itoh | |
| 5,684,583 A | 11/1997 | Abe et al. | |
| 5,793,485 A * | 8/1998 | Gourley ......................... 356/318 |
| 2004/0008345 A1* | 1/2004 | Nurmikko et al. ............ 356/318 |
| 2008/0158561 A1* | 7/2008 | Vacca et al. ................... 356/338 |

FOREIGN PATENT DOCUMENTS

| | | |
|---|---|---|
| EP | 0 681 178 | 11/1995 |
| JP | 01-270644 | 10/1989 |
| JP | 02-221843 | 9/1990 |
| JP | 03-172736 | 7/1991 |
| JP | 2007-046947 | 2/2007 |
| WO | 2006/115663 | 11/2006 |
| WO | 2008/082813 | 7/2008 |

OTHER PUBLICATIONS

Japanese Office Action issued on Sep. 8, 2009, for corresponding Japanese Patent Application JP 2007-228932.

* cited by examiner

*Primary Examiner* — Kara E Geisel
(74) *Attorney, Agent, or Firm* — K&L Gates LLP

(57) ABSTRACT

A light irradiation method of irradiating a specimen in a flow channel with directional light includes the step of irradiating the specimen with the directional light while performing scanning using the directional light in a widthwise direction of the flow channel. The directional light has an irradiation spot that is smaller than a width of the flow channel. Accordingly, energy density of the irradiation spot can be increased without increasing output power of a light source.

14 Claims, 5 Drawing Sheets

(R STATE)

LIGHT IRRADIATION METHOD, LIGHT IRRADIATION DEVICE, AND FINE PARTICLE ANALYZING APPARATUS

CROSS REFERENCES TO RELATED APPLICATIONS

The present application claims priority to Japanese Patent Application JP 2007-228932 filed in the Japanese Patent Office on Sep. 4, 2007, the entire contents of which is incorporated herein by reference.

BACKGROUND

The present application relates to a light irradiation method, a light irradiation device, and a fine particle analyzing apparatus. More specifically, the present application relates to a technology of irradiating a specimen in a flow channel with directional light.

An irradiation technology using directional light, such as laser light, is widely used in, for example, spectral measurement or a processing technology. Directional light has uniform wavelength and phase. Therefore, when the directional light is converged using, for example, a lens, the light can be converged at a small point, so that energy density at an irradiation point of the directional light is high.

Laser spectroscopy can be classified into, for example, linear laser spectroscopy and nonlinear laser spectroscopy. The linear laser spectroscopy that measures an absorption spectrum or an excitation spectrum also provides a high sensitivity and a high resolution compared to a related spectroscopy using a light source. The non-linear spectroscopy can provide a higher sensitivity and resolution. Examples of laser spectroscopy include laser-induced fluorescence spectroscopy, laser Raman spectroscopy, Coherent anti-Stokes Raman Scattering (CARS), polarization spectroscopy, resonance ionization spectroscopy, and photoacoustic spectroscopy. In particular, spectroscopy having a high time resolution is called picosecond spectroscopy or femtosecond spectroscopy.

For example, the laser irradiation technology is also used in flow cytometry (refer to "Cell Technology Supplementary Volume: Experiment Protocol Series, Flow Cytometry With Flexibility," by Hiromitsu Nakauchi, Published in Aug. 31, 2006 by Shujunsha, Second Edition, pp. 12 to 13). "Flow cytometry" refers to a measurement method in which a cell (a measurement object to be measured) is sorted while it is alive, to analyze, for example, the function of the cell. The cell is caused to flow into a laminar flow, to irradiate the cell passing a flow cell with laser. Fluorescent light or scattering light, which is generated by the irradiation, is measured. In a pulse detecting system, fluorescent light or scattering light, generated when the cell traverses the laser, is detected as an electrical pulse. Then, for example, a pulse height, a pulse width, or a pulse area is analyzed to analyze, for example, the function of the cell. This makes it possible to analyze the characteristics of each living cell by detecting scattering light or fluorescent light, generated from each cell.

SUMMARY

When, for example, irradiation is not sufficiently and reliably performed due to a change in the position of a specimen in a flow channel, the diameter of an irradiation spot of irradiation light is made larger than the width of the flow channel. However, this gives rise to a problem in that an output power of a light source must be raised due to a reduction in the energy density of the irradiation spot.

Accordingly, it is desirable to provide a light irradiation method that can relatively increase energy density of an irradiation spot without increasing the output power of a light source.

According to an embodiment, there is provided a light irradiation method of irradiating a specimen in a flow channel with light. The method includes the step of irradiating the specimen with the light while performing scanning using the light in a widthwise direction of the flow channel. The light has an irradiation spot that is smaller than a width of the flow channel.

Scanning with the irradiation spot of the irradiation light in the widthwise direction of the flow channel makes it possible to at least relatively increase energy density of the irradiation spot of the irradiation light. As a result, it is possible to reduce output power of a light source and to increase a light-converging efficiency of the irradiation light.

In the light irradiation method, the light irradiation may be performed while performing the scanning with at least any of a galvanometer, an electro-optical element, a polygon mirror, and an MEMS element.

In the light irradiation method, the scanning using the directional light may be performed under a condition satisfying the following Expression (1):

$$\frac{D_2}{v_1} > \frac{D_1}{v_2} \qquad (1)$$

where $v_1$ is a speed of movement of the specimen in the interior of the flow channel, $v_2$ is a scanning speed of the directional light, $D_1$ is the width of the flow channel, and $D_2$ is a diameter of the irradiation spot.

Scanning under such a condition makes it possible for the specimen to traverse a scanning spot at least once within a time in which the scanning spot passes the width of the flow channel. As a result, the specimen in the interior of the flow channel can be detected with the scanning spot.

According to another embodiment, there is provided a light irradiation device that irradiates a specimen in a flow channel with light. The device includes at least a light source and a scanner. The light source is used to perform the irradiation with the light having an irradiation spot that is smaller than a width of the flow channel. The scanner performs scanning using the light in a widthwise direction of the flow channel. When the light irradiation device includes the scanner, the light irradiation device is one that reduces the output power of the light source and increases the light-converging efficiency of the irradiation light.

According to still another embodiment, there is provided a fine particle analyzing apparatus including the above-described light irradiation device.

According to an embodiment, it is possible to relatively increase the energy density of the irradiation spot of the light irradiation without increasing the output power of the light source.

Additional features and advantages are described herein, and will be apparent from the following Detailed Description and the figures.

DETAILED DESCRIPTION

A light irradiation method, a light irradiation device, and a fine particle analyzing apparatus according to an embodiment will be described in detail below with reference to the attached drawings. The embodiments depicted in the attached drawings are illustrative thereof and thus should not to be interpreted as narrowing the scope of the present application.

Figure 1:
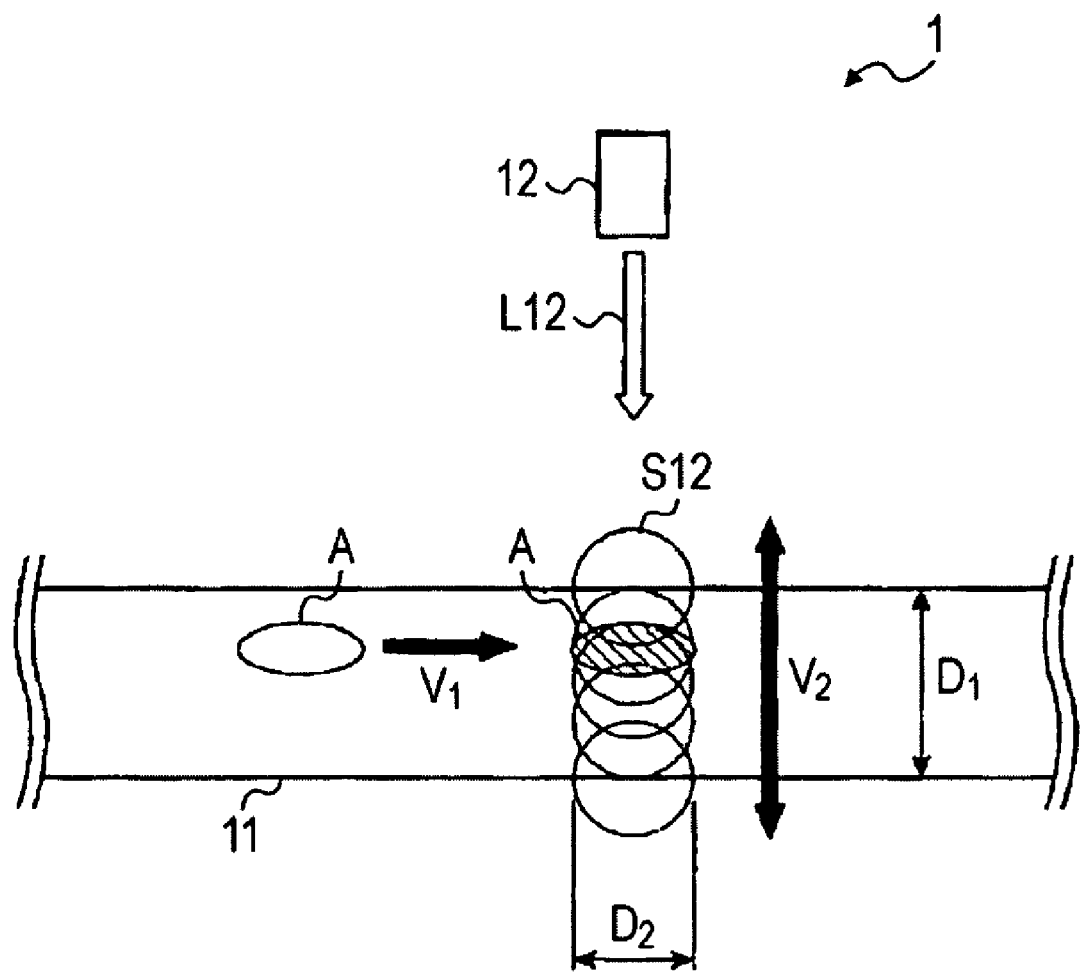
FIG. 1 is a schematic view of a light irradiation method and a light irradiation device according to an embodiment.
Figure 1:
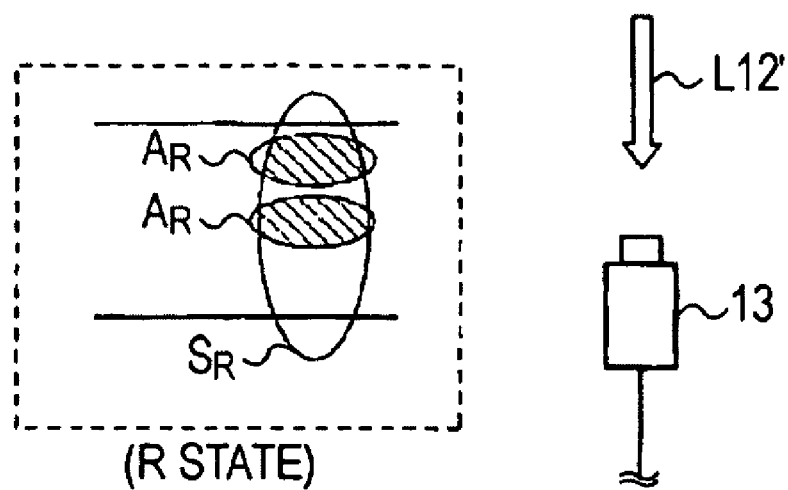

FIG. 1 is a schematic view of a light irradiation method and a light irradiation device according to an embodiment.

In FIG. 1, reference numeral 1 denotes a light irradiation device. The light irradiation device 1 includes a flow channel 11 and a light source 12. Reference character A denotes a specimen, which is an irradiation object. Reference character S denotes an illumination spot of irradiation light used for irradiation. The specimen A exists in the interior of the flow channel 11, and moves at a speed $v_1$. Performing scanning with directional light L12 at a speed $v_2$ provides a plurality of irradiation spots S12.

In an embodiment, the type of specimen A existing in the interior of the flow channel 11 is not limited. For example, the specimen A may be a cell or a fine particle, such as a bead. A medium in the interior of the flow channel 11 is a fluid, so that, for example, various solutions or gases may be used. A suitable medium may be selected considering, for example, an irradiation condition or the type of specimen A.

Forming the plurality of irradiation spots S12 as a result of light scanning makes it possible to perform the scanning at predetermined positions of the flow channel 11. Therefore, no matter where the specimen A exists in the interior of the flow channel 11, the interior of the flow channel 11 can be irradiated and scanned with light at a high speed.

The type of directional light L12 emitted from the light source is not particularly limited, so that, for example, laser or a light emission diode (LED) may be used.

When laser is used as the directional light L12, its medium may be, for example, a semiconductor laser, a liquid laser, a gas laser, or a solid laser.

Examples of semiconductor lasers include a GaAs laser and an InGaAsP laser. Examples of gas lasers include an He—Ne laser (red), an Ar laser (visible, blue, green), a $CO_2$ laser (infrared), and an excimer laser (purple, etc.). An example of a liquid laser is a dye laser. Examples of solid lasers include a ruby laser, a YAG laser, and a glass laser. A Diode-Pump Solid-State Laser (DPSS) that is a laser diode (LD) that pumps and oscillates a solid-state medium, such as Nd:YAG, may also be used.

The purpose for which light irradiation is performed in an embodiment is not limited, so that a suitable light source 12 can be selected as appropriate in accordance with the purpose. For example, the light irradiation may be performed for, for example, various analyses, measurements, heating operations, or processings.

For example, when analyses or measurements are to be performed, a detector 13 may be used for detecting a measurement light L12' obtained by irradiating the specimen A with the directional light L12. Although not shown, the detector 13 includes an analog-digital converter (ADC) to convert the detected measurement light L12' into a digital signal and to perform a computation with, for example, a central processing unit (CPU) (not shown).

The type of measurement light L12' is not limited. A suitable detecting method may be used as appropriate considering the type of specimen A or a measurement condition. Examples of measurement lights include scattering light and fluorescent light emitted from the specimen A. In a detecting method, for example, the specimen A is previously labeled with a particular fluorescent material, and is irradiated with the light L12, which is pump light, from the light source 12. The fluorescent light emitted due to the irradiation is detected as the measurement light 12'.

When fluorescent dye is used, the light L12 emitted from the light source 12 is used as directional light, and fluorescent dye corresponding the wavelength of the light L12 (for example, laser wavelength) may be used.

When an Ar ion laser (488 nm) is used, for example, fluorescein isothiocyanate (FITC), phycoerythrin (PE), peridinin chlorophyll protein (PerCP) may be used for the fluorescent dye. When an He—Ne laser (633 nm) is used, for example, allophycocyanin (APC) or APC-Cy7 may be used for the fluorescent dye. When a dye laser (598 nm) is used, for example, Texas Red (TR) may be used for the fluorescent dye. When a Cr laser (407 nm) or a semiconductor laser is used, for example, Cascade Blue may be used for the fluorescent dye.

In a different detecting method using a measurement light, scattering light (forward scattering light or lateral scattering light) from the specimen A can be detected without, for example, labeling. For example, scattering light emitted when the irradiation spot S12 passes the specimen A may be detected. In this case too, when the light L12 is directional light, positional information can be detected with higher precision.

When the specimen A moves in the interior of the flow channel 11, the position of the specimen A in the interior of the flow channel 11 changes. In particular, when the size of the specimen A is considerably smaller than a flow-path width $D_1$ of the flow channel 11, the specimen A moves in the interior of the flow channel 11 with a certain degree of freedom. Therefore, for example, a considerable irradiation unevenness, positional displacement of irradiation, or positional displacement of focusing may occur. These factors are part of the reason for a reduction in irradiation efficiency of the directional light L12. Accordingly, in the past, for example, the irradiation time has been made long, or an irradiation spot diameter $D_2$ has been made larger than the flow channel width $D_1$ (refer to an R state in FIG. 1). Although, in, for example, the R state (serving as a related example), substantially an entire area of a specimen $A_R$ can be irradiated, an irradiation spot $S_R$ becomes large. Therefore, a beam output is increased. In addition, for example, the irradiation spot $S_R$ is formed into a predetermined elliptical shape.

In contrast, in an embodiment, the irradiation is performed while performing scanning using the directional light L12 (refer to $v_2$ in FIG. 1). By forming the plurality of irradiation spots S12 in the interior of the flow channel 11, the specimen A passes at least any of the illumination spots S12. Therefore, even if the irradiation spot diameter $D_2$ of the irradiation spot S12 is not made large, the specimen A moving in the interior of the flow channel 11 can be sufficiently and precisely irradiated with the light.

The scanning using the directional light L12 is not limited to that at a constant speed, so that the scanning can be performed as appropriate at a variable speed considering, for example, the purpose of use or an irradiation condition. However, it is desirable to perform the scanning at a high speed. This makes it possible to more reliably irradiate the specimen A moving through the flow channel 11 with the light, and to perform light irradiation a plurality of times. In particular, it is desirable to perform light irradiation under the condition of the following Expression (1):

$$\frac{D_2}{v_1} > \frac{D_1}{v_2} \quad (1)$$

where $v_1$ is the speed of movement of the specimen in the interior of the flow channel, $v_2$ is the scanning speed of the directional light, $D_1$ is the width of the flow channel, and $D_2$ is the diameter of the irradiation spot.

In the left side of Expression (1), "irradiation spot diameter $D_2$" is divided by "movement speed $v_1$ of the specimen A in the interior of flow channel 11." This approximates to the time in which the specimen A passes the diameter of the irradiation spot. Although the irradiation spot diameter $D_2$ is not particularly limited, it is desirable that it be in the range of from 1 μm to 100 μm. Although the movement speed $v_1$ of the specimen A through the flow channel 11 is not particularly limited, it is desirable that it be in the range of from 0.1 m/s to 10 m/s.

In the right side of Expression (1), "flow channel width $D_1$" is divided by "scanning speed $v_2$ of directional light." This approximates to the scanning time for scanning the flow channel width with the directional light. Although the flow channel width $D_1$ is not particularly limited, it is desirable that it be in the range of from 10 μm to 1 mm. Although the scanning speed $v_2$ of the directional light is not particularly limited, it is desirable that it be in the range of from 1 m/s to 50 m/s.

That is, when the specimen A passes the irradiation spot diameter, the entire width of the flow channel is irradiated with the light at least once. Therefore, for performing scanning by a larger number of times, it is desirable that ($D_2/v_1$) be sufficiently larger than ($D_1/v_2$). More specifically, it is desirable that ($D_2/v_1$) be 2 to 10 times ($D_1/v_2$). In this case, scanning can be performed 2 to 10 times while the specimen A passes the irradiation spot S12. This makes it possible to increase the efficiency with which the directional light L12 is used. By integrating detection signals based on a plurality of scanning operations, an S/N ratio of the directional light L can be further increased. For example, when using light, such as fluorescent light, for handling something that is relatively dark, noise can be reduced while increasing a fluorescent-light signal. Therefore, this is particularly desirable.

In addition to performing scanning at a high speed, a similar effect can be obtained even by further reducing the flow channel width $D_1$. Reducing the flow channel width $D_1$ makes it possible to reduce the scanning time (that is, $D_1/v_2$) of the irradiation spot S12. Setting such a scanning condition and a flow channel structure makes it possible to perform light irradiation a plurality of times with respect to the specimen. For example, if light irradiation can be performed an N number of times, integrating signals thereof makes it possible to increase the S/N ratio of the detection light signal by a factor of $(N)^{1/2}$.

The scanner used in light irradiation is not particularly limited. However, it is desirable to perform scanning with the irradiation spot S12 using, for example, a galvanometer mirror, an electro-optical element, a polygon mirror, or an MEMS element. In particular, since an electro-optical element does not include a movable section, it is a desirable to use the electro-optical element from the view points of particularly high stability and reliability. A plurality of the scanners may also be used.

The light irradiation device 1 according to an embodiment may be one including at least the light source 12 and a scanner. The light source 12 is used for irradiation with the directional light L12 having the irradiation spot $D_2$ that is smaller than the flow channel width $D_1$ of the flow channel 11. The scanner performs scanning using the directional light L12 in the widthwise direction of the flow channel. The light irradiation device 1 may further include an optical detecting system that detects the measurement light L12' generated in the irradiation spot S12.

Figure 2:
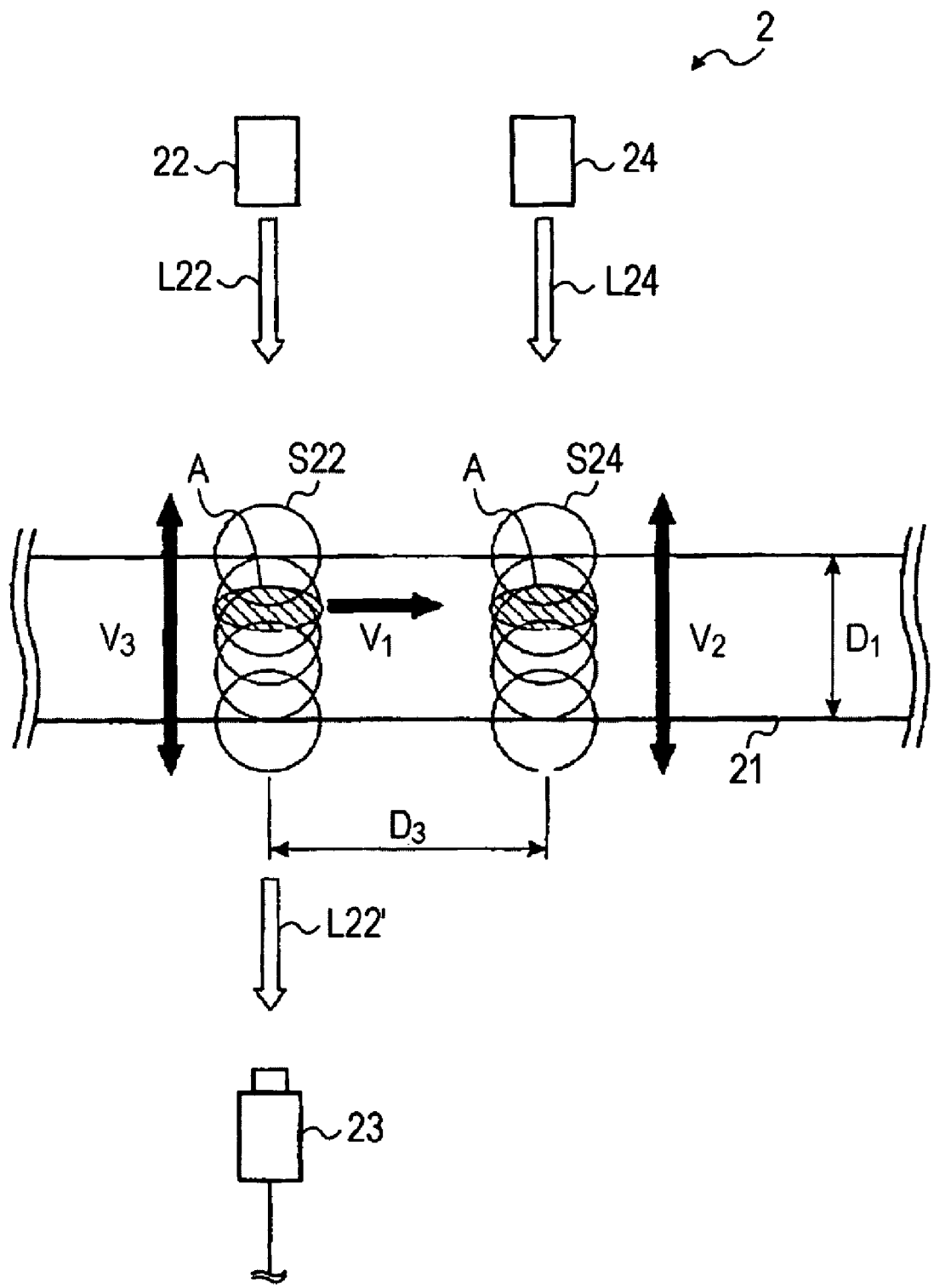
FIG. 2 is a schematic view of a light irradiation method and a light irradiation device according to another embodiment.

FIG. 2 is a schematic view of a light irradiation method and a light irradiation device according to another embodiment. In FIG. 2, reference numeral 2 denotes the light irradiation device.

In the light irradiation method and the light irradiation device 2 shown in FIG. 2, a specimen A transported into a flow channel 21 is irradiated with light L22 emitted from a light source 22 and used for obtaining positional information. A description will hereunder be given focusing on the differences between the light irradiation method and device shown in FIG. 2 and those shown in FIG. 1.

The specimen A moves in the interior of the flow channel 21 at a speed $v_1$. The specimen A is irradiated with light L22 for obtaining positional information from the light source 22. Performing scanning with an irradiation spot S22 causes the specimen A passing the irradiation position to be reliably irradiated with the light. When a detector 23 detects a measurement light L22' generated by the irradiation, the positional information of the specimen A can be obtained.

On the basis of this positional information, directional light L24 from a following light source 24 illuminates an irradiation spot S24. The irradiation spot 24 is used for scanning as in the light irradiation method shown in FIG. 1, but allows scanning of the specimen A to be started on the basis of the positional information. That is, it is possible to confirm the position of the specimen A at the irradiation spot S22 (refer to a corresponding shaded area in FIG. 2), and to predict the position of the specimen A in the irradiation spot S24 from such positional information (refer to a corresponding shaded area in FIG. 2).

Obtaining the positional information makes it possible to control a timing in which the specimen A is irradiated with the directional light L24 at the irradiation spot S24. That is, it is possible to predict the time in which the specimen reaches the irradiation spot S24 from the irradiation spot S22. For example, the time can be set so that light irradiation is performed from the light source 24 after passage of ($D_3/v_1$) subsequent to the irradiation with the light L22 used to detect the positional information.

In an embodiment, the timing can be controlled so that the directional light L24 is used for irradiation when the specimen A reaches the irradiation spot S22. In this case, since the directional light L24 from the light source 24 is not used for a long time or for continuous irradiation, it is possible to contribute to, for example, an increase in the life of the light source 24 or a reduction in the burden on the device.

Irradiating a plurality of the illumination spots S24 with the light L22 for obtaining the positional information makes it possible not only to detect the passage of time of the specimen A at this position, but also to detect the positional information. As a result, it is possible to perform irradiation with the following directional light L24 with higher precision. In addition, it is possible to select optimal conditions for an irradiation timing and an irradiation scanning start position, so that the light irradiation can be efficiently performed.

In addition, when a process, such as a treatment, a processing, or sorting of the specimen, is performed at areas other than in the interior of the flow channel, the obtained positional information or speed information can be used as a trigger signal for such a process. That is, it is possible to output as a signal the positional information of the specimen, obtained by the light irradiation, to portions of a device for performing a separate operation, so that the positional information can be used as a trigger signal for the portions of the device.

Obtaining the positional information of the specimen A in the interior of the flow channel 21 in this way makes it possible to adjust and optimize, for example, the irradiation position, the irradiation time, or the irradiation strength of the directional light L24 from the light source 24. As a result, it is possible to further mitigate, for example, defocusing, an irradiation shift, or an uneven irradiation at the irradiation spot S24.

The method of irradiating a plurality of irradiation spots S22 with the light L22 for obtaining the positional information is not limited, so that a plurality of light sources 22 corresponding to the respective irradiation spots S22 may be provided. However, it is desirable to perform scanning using the light L22 emitted from one light source 22. When a scanning mechanism is used, only one light source 22 is used, so that the structure of the device can be simplified.

The positional information of the specimen A refers to information regarding, for example, the position or the flow speed of the specimen existing in the interior of the flow channel 21, and includes various items of information regarding vectors of the specimen A in the interior of the flow channel 21. In an embodiment, only information to be used as positional information is detected, so that the positional information is not limited.

Although not illustrated, as a detector that detects positional information, it is possible to separately provide a controller that controls irradiation using directional light on the basis of positional information obtained by detecting the measurement light L22' with the detector 23. For example, it is possible to convert measurement data of the measurement light L22' detected with the detector 23 into a digital signal with, for example, an analog-digital converter (ADC), perform a computation on this signal with a computer, and feed back the signal as information for controlling irradiation with the light source 24.

The type of measurement light L22' is not limited. A suitable detecting method may be used as appropriate considering, for example, the type of specimen A or a measurement condition. Examples of measurement lights include scattering light and fluorescent light emitted from the specimen A. In a detecting method, as mentioned above, the specimen A is previously labeled with a particular fluorescent material, and is irradiated with the light L22, which is used as pump light, from the light source 22. The fluorescent light emitted due to the irradiation is detected as the measurement light L22'. In addition, the scattering light emitted from the specimen A can be detected as positional information without performing the labeling.

A system that reflects the positional information is not limited to the optical system that performs light irradiation. For example, it is possible to provide a controller that controls fluid speed of a medium in the interior of the flow channel 21 (that is, the movement speed $v_1$ of the specimen A) considering the positional information of the specimen (in particular, for example, the movement speed). Adjusting the fluid speed of the medium in the interior of the flow channel 21 on the basis of the positional information makes it possible to precisely irradiate the specimen A with the directional light L24.

When the medium is irradiated while performing scanning with the light L22 for obtaining the positional information, a scanning condition is not particularly limited. However, it is desirable that the scanning be performed at a high speed. This makes it possible to reliably irradiate the specimen A moving in the interior of the flow channel 11 with the light. Due to the same reason as in the Expression (1), it is particularly desirable to carry out the light irradiation under the condition of the following Expression (2):

$$\frac{D_4}{v_1} > \frac{D_1}{v_3} \qquad (2)$$

where $v_1$ is the speed of movement of the specimen in the interior of the flow channel, $v_3$ is the scanning speed of light for obtaining positional information, $D_1$ is the width of the flow channel, and $D_4$ is the diameter of the irradiation spot S22 for obtaining positional information.

Therefore, the light irradiation device according to an embodiment may be one further including the light source 22, a scanner, and an optical detecting system. The light source 22 is used to perform irradiation with the light L22, used for obtaining the positional information of the specimen A, in the flow channel 21. The scanner performs scanning using the light L22 for obtaining the positional information. The optical detecting system detects the measurement light 22' that is emitted as a result of irradiation of the specimen A with the light L22 for obtaining the positional information.

A calculation processor and an irradiation controller may be further provided. The calculation processor performs a calculation processing operation on measurement data obtained with the optical detecting system, to obtain the measurement data as positional information. The irradiation controller controls the irradiation using the directional light L24 on the basis of the positional information. Further, it is desirable that the irradiation spot diameter $D_4$ of the light L22 for obtaining the positional information be smaller than the flow channel width $D_1$ of the flow channel 22. This makes it possible to simplify the structure of the device, and to reduce the number of light sources, so that the device can become an economical device, and the maintenance of the device can be reduced.

Figure 3:
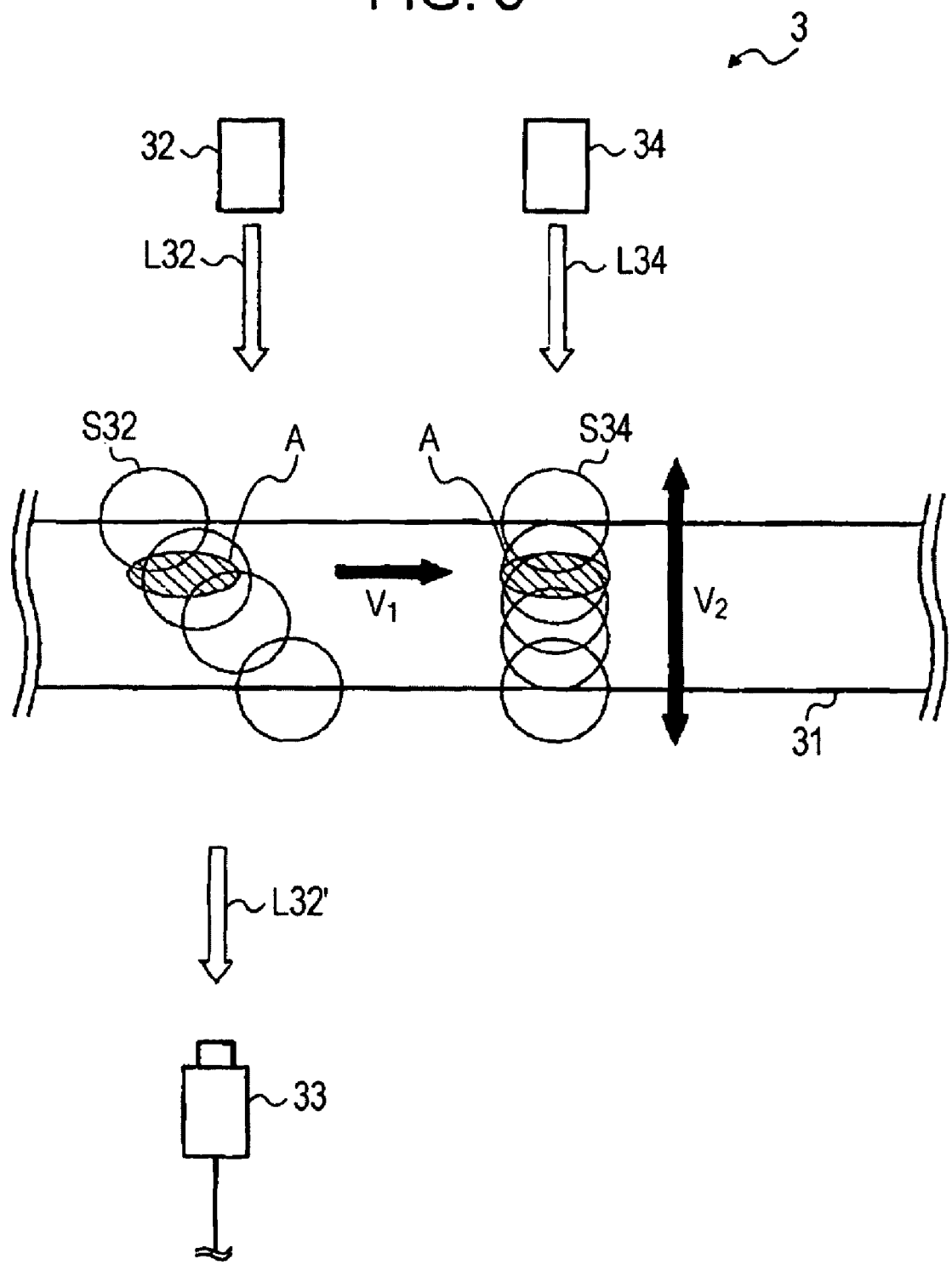
FIG. 3 is a schematic view of a light irradiation method and a light irradiation device according to still another embodiment.

FIG. 3 is a schematic view of a light irradiation method and a light irradiation device according to still another embodiment. In FIG. 3, reference numeral 3 denotes the light irradiation device.

One feature of the light irradiation method and the light irradiation device 3 shown in FIG. 3 is that, with respect to a specimen A transported in the interior of a flow channel 31, different positions in a flow channel direction and a widthwise direction are irradiated with an irradiation spot S32 of light for obtaining positional information. A description will hereunder be given focusing on the differences between the light irradiation method and device shown in FIG. 3 and those shown FIGS. 1 and 2.

The specimen A moves at a speed $v_1$ in the interior of the flow channel 31. Light L32 for obtaining positional information is emitted from a light source 32 with respect to the specimen A. The irradiation spot S32 is used to perform scanning in the flow channel direction (X direction) and the widthwise direction (Y direction). When a detector 33 detects measurement light L32' emitted from the specimen A passing the irradiation spot S32, positional information of the specimen A can be obtained. In addition, on the basis of the positional information, directional light 34 from a light source 34 illuminates an irradiation spot S34.

In particular, performing the scanning with the irradiation spot S32 in the flow channel direction (X direction) and the widthwise direction (Y direction) makes it possible to obtain positional information of the specimen A with a time difference. As a result, it is possible to more precisely know where the specimen A exists in the flow channel 31 in the flow-path direction and the widthwise direction. Obviously, the detection of light is not limited to two-dimensional detection (that is, in the flow channel direction and the widthwise direction), so that scanning can be performed so as to detect three-dimensional positional information (including depth direction (Z direction) positional information).

Figure 4:
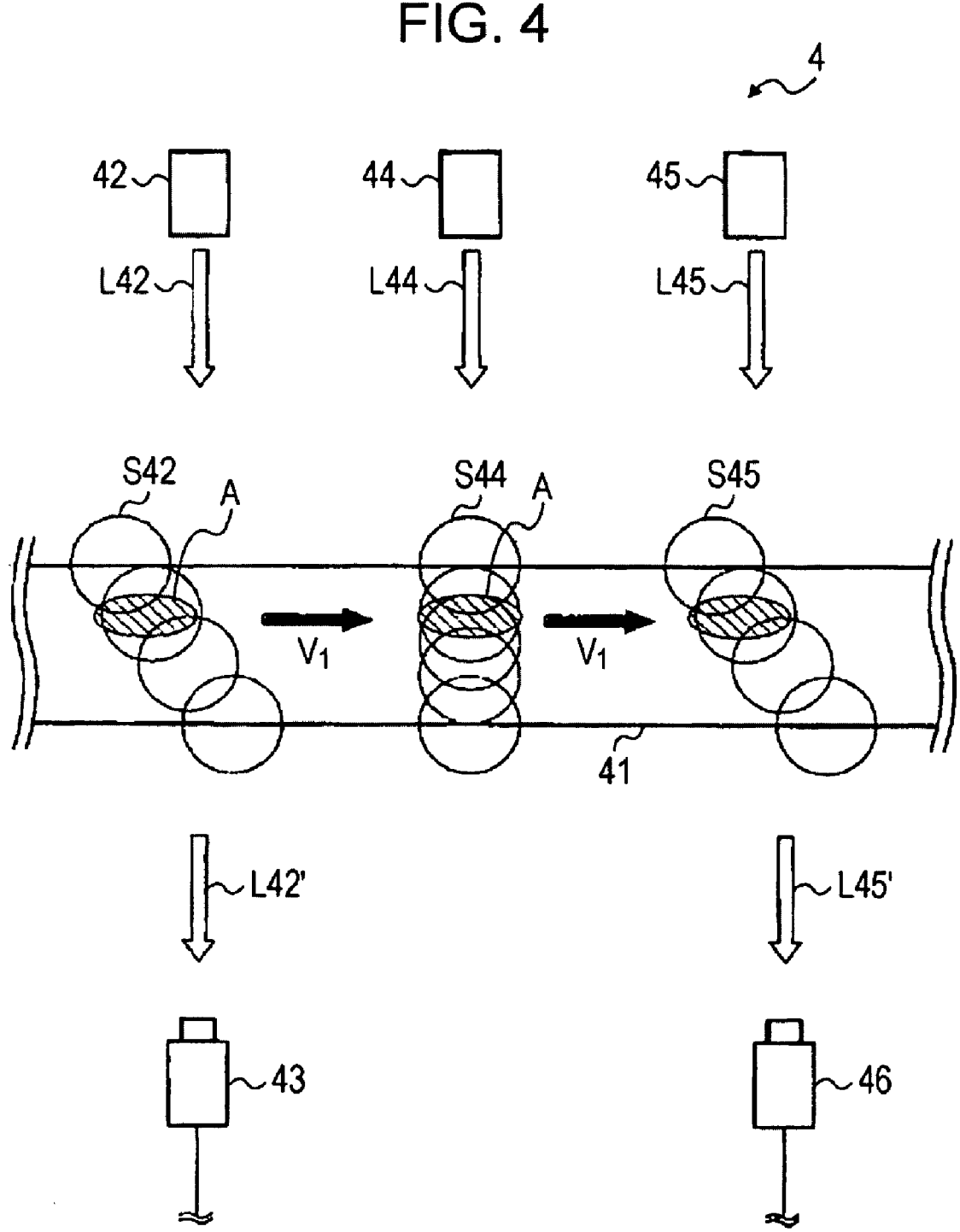
FIG. 4 is a schematic view of a light irradiation method and a light irradiation device according to still another embodiment.

FIG. 4 is a schematic view of a light irradiation method and a light irradiation device according to still another embodiment. In FIG. 4, reference numeral 4 denotes the light irradiation device.

One feature of the light irradiation method and the light irradiation device 4 shown in FIG. 4 is that irradiation spots S42 and S45 of lights L42 and L45 for obtaining positional information are provided on the front and back sides of an irradiation spot S44 of directional light L44. A description will hereunder be given focusing on the differences between the light irradiation method and device shown in FIG. 4 and those shown in FIGS. 1 to 3.

A specimen A moves at a speed $v_1$ in the interior of a flow channel 41. Light L42 for obtaining positional information is emitted from a light source 42 with respect to the specimen A, to detect measurement light L42' with a detector 43. Then, directional light L44 from a light source 44 illuminates the specimen A while performing scanning using the directional light L44 in a widthwise direction of the flow channel. Thereafter, light L45 for obtaining again positional information is emitted from a following light source 45, to detect measurement light L45' with a detector 46.

When the light L45 for obtaining positional information illuminates the irradiation spot S45 after irradiating the irradiation spot S44 with the directional light L44, it is possible to know, for example, where the specimen A exists at a rear area of the flow channel 41. Even if the measurement light L42' at the front irradiation spot S42 is not sufficiently detected, the measurement light L45' at the rear irradiation spot S45 can be detected, so that more detailed position information can be obtained. Accordingly, the positional information of the specimen A at the rear area of the flow channel 41 can reflect, for example, light irradiation with the directional light L44.

Providing at a plurality of locations the irradiation spots of light for obtaining positional information makes it possible to obtain the positional information of the specimen A with higher precision. In particular, when the specimen A can move with a certain degree of freedom in the interior of the flow channel 41, it is possible to perform advanced light irradiation as a result of obtaining positional information prior to irradiation with the directional light L44 and positional information after irradiation with the directional light L44.

Figure 5:
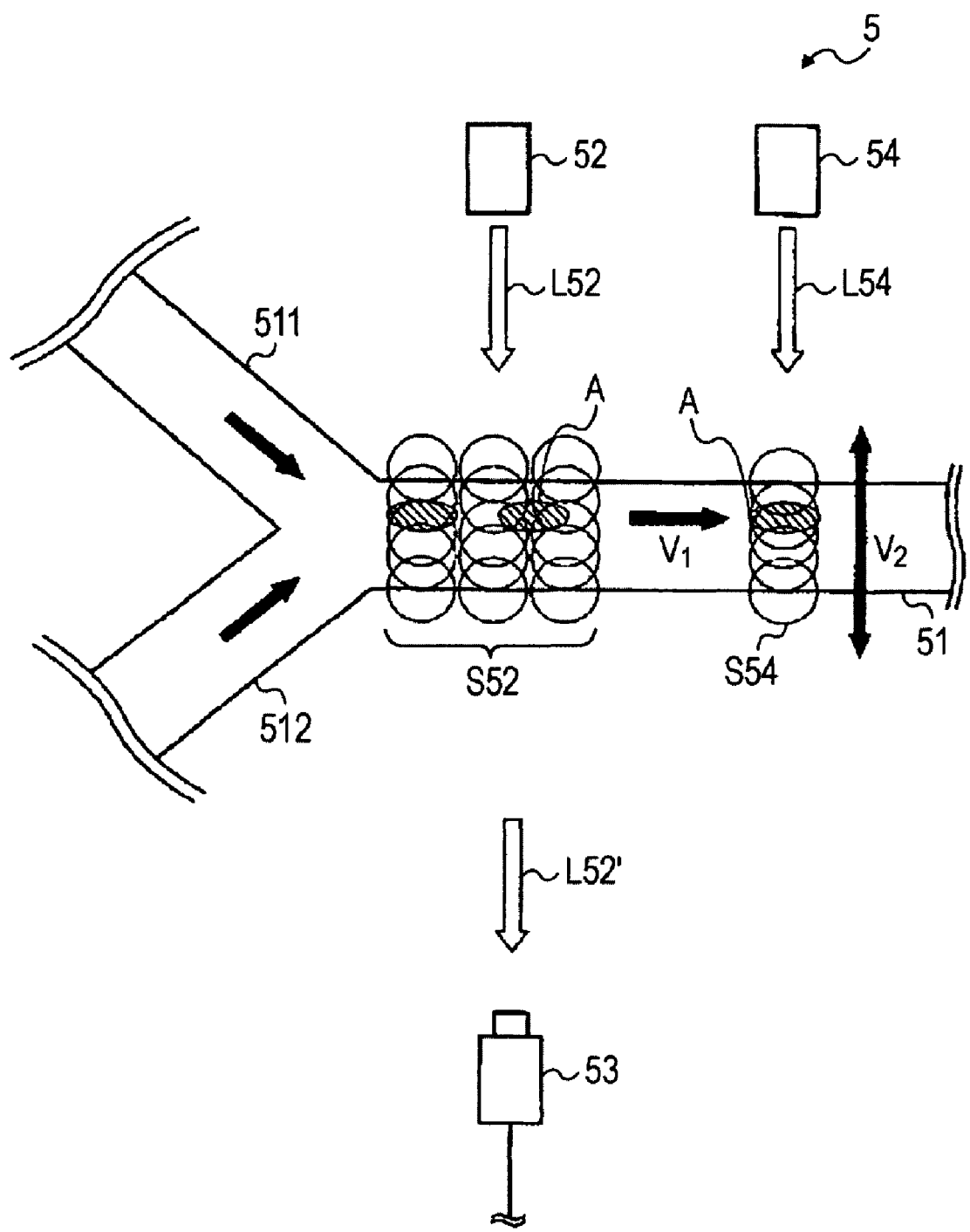
FIG. 5 is a schematic view of a light irradiation method and a light irradiation device according to still another embodiment.

FIG. 5 is a schematic view of a light irradiation method and a light irradiation device according to still another embodiment. In FIG. 5, reference numeral 5 denotes the light irradiation device.

One feature of the light irradiation method and the light irradiation device 5 shown in FIG. 5 is that irradiation spots for light irradiation for obtaining position information are provided at the front and back of an irradiation spot of directional light. A description will hereunder be given focusing on the differences between the light irradiation method and device shown in FIG. 5 and those shown in FIGS. 1 to 4.

A flow channel 51 has a substantially Y-shaped flow channel structure. That is, specimens A transported from flow channels 511 and 512 meet and are transported to an irradiation position. Light L52 for obtaining positional information and emitted from a light source 52 illuminates irradiation spots S52 at nine locations. Measurement light L52' emitted due to the irradiation is detected with a detector 53, to obtain positional information. On the basis of the obtained positional information, directional light L54 emitted from a light source 54 illuminates an irradiation spot S54.

When the irradiation spots S52 of light for obtaining position information illuminate a plurality of locations in the interior of the flow channel 51, a more detailed positional information of the specimen A can be detected. In particular, when irradiation with the light L52 for obtaining positional information is performed with respect to respective substantially box-shaped divided areas in the flow channel 51, a more precise positional information can be obtained.

When, for example, the flow channel 51 is branched, the specimen A is transported to the irradiation spots S52 while moving violently as a result of, for example, colliding at the merging area in the flow channel 51. By providing a large number of irradiation spots S52 of the light L52 for obtaining positional information, and irradiating the specimen A so as to include the space in the interior of the flow channel 51, it is possible to obtain in detail the positional information of the specimen A with time. As a result, more precise positional information can be detected.

Although not illustrated, when, for example, the specimen A is sorted at the back portion of the flow channel 51, the positional information can be used for, for example, determining what location in the flow channel 51 the specimen exists and at what speed the specimen moves to the following sorting predetermined position.

For example, the embodiment is suitable when different specimens are made to pass through the flow channels 511 and 512 so as to be used as micro-reactors. The embodiment can be performed when some kind of reaction progresses due to the merging of the flow channels 511 and 512, and a subsequent reactant is irradiated with the directional light 54 to perform spectral detection, and sampling is performed in accordance with a result of the spectral detection.

The light irradiation methods and light irradiation devices according to an embodiment are applicable to various technical fields. For example, they may be applied to measuring devices/analyzing devices using directional light, such as a particle diameter distribution measuring device, a fluid image analyzing device, a three-dimensional measuring device, and a laser microscope. For a technology that irradiates a specimen in a flow channel, they are suitably used in, for example, a fine particle analyzing device that measures very small particles among such measuring devices/analyzing devices.

Examples of fine particle analyzing devices include a flow cytometry analyzing device and a bead assay (flow bead assay) device. That is, the light irradiation methods and light irradiation devices according to an embodiment are applicable to a technology that, for example, sorts fine particles as a result of irradiating the fine particles with light and detecting obtained measurement light, such as fluorescent light or scattering light.

Examples of flow cytometry analyzing devices include a device for measuring, for example, the structure and size of fine particles and a device that is formed so as to sort predetermined fine particles on the basis of, for example, the measured size and structure. Among these devices, the device that samples cells can be used as a cell sorter. The cell sorter can sample and measure several tens of thousands of to 100,000 cells every second at a high speed. In particular, even fine particles can be precisely irradiated with light.

When fine particles are to be sorted, the light irradiation device according to any embodiment can be used as an optical detecting mechanism. That is, since precise positions of the fine particles (such as living cells) in the flow channel can be irradiated with laser, even, for example, a very small number of stem cells existing in the living cells can be precisely and efficiently sorted.

Since suitable laser irradiation which is, for example, rarely omitted can be performed on fine particles (such as cells or beads) in the flow channel, the detection can be performed with higher precision. In addition, the light irradiation device can be formed as a fine particle analyzing device that can perform a real-time detection.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A light irradiation method of irradiating a specimen moving through a flow channel with directional light, the method comprising:
   irradiating the specimen with the directional light from a first light source while performing scanning using the directional light in a widthwise direction of the flow channel, the directional light having an at least substantially circular irradiation spot having a diameter that is smaller than a width of the flow channel,
   obtaining positional information of the specimen prior to irradiating the specimen with the directional light by performing scanning of the specimen with a second irradiation spot from a second light source, and detecting a measurement light that is generated by the irradiation of the specimen by the second light source,
   wherein irradiating the specimen with the directional light at a given time is based on the obtained positional information of the specimen, and
   wherein scanning is performed in the widthwise direction of the flow channel at a single position in a flow channel direction a plurality of times during a period of time when the specimen moves through an area irradiated by the irradiation spot.

2. The method according to claim 1, wherein the scanning using the directional light is performed with at least any of a galvanometer, an electro-optical element, a polygon mirror, and an MEMS element.

3. The method according to claim 1, wherein the scanning using the directional light is performed under a condition satisfying the following Expression (1):

$$\frac{D_2}{v_1} > \frac{D_1}{v_2} \quad (1)$$

where $v_1$ is a speed of movement of the specimen in the interior of the flow channel, $v_2$ is a scanning speed of the directional light, $D_1$ is the width of the flow channel, and $D_2$ is a diameter of the irradiation spot.

4. A light irradiation device that irradiates a specimen moving through a flow channel with directional light, the device comprising at least:
   a first light source used to perform the irradiation with light having an at least substantially circular irradiation spot having a diameter that is smaller than a width of the flow channel;
   a first scanning means for performing scanning using the light from the first light source in a widthwise direction of the flow channel,
   a second light source;
   a second scanning means for performing scanning of the specimen with a second irradiation spot from the second light source, and
   a detector used to detect a measurement light that is generated by the irradiation of the specimen by the second light source,
   wherein the measurement light is used to obtain positional information of the specimen prior to irradiating the specimen with the directional light;
   wherein irradiating the specimen with the directional light at a given time is based on the obtained positional information of the specimen, and
   wherein the first scanning means performs scanning in the widthwise direction of the flow channel at a single position in a flow channel direction a plurality of times during a period of time when the specimen moves through an area irradiated by the irradiation spot.

5. A fine particle analyzing apparatus comprising:
   the light irradiation device according to claim 4.

6. A light irradiation device that irradiates a specimen moving through a flow channel with directional light, the device comprising at least:
   a first light source used to perform the irradiation with light having an at least substantially circular irradiation spot having a diameter that is smaller than a width of the flow channel;
   a first scanner that performs scanning using the light from the first light source in a widthwise direction of the flow channel,
   a second light source;
   a second scanner for performing scanning of the specimen with a second irradiation spot from the second light source, and
   a detector used to detect a measurement light that is generated by the irradiation of the specimen by the second light source,
   wherein the measurement light is used to obtain positional information of the specimen prior to irradiating the specimen with the directional light;
   wherein irradiating the specimen with the directional light at a given time is based on the obtained positional information of the specimen, and
   wherein the first scanner performs scanning in the widthwise direction of the flow channel at a single position in a flow channel direction a plurality of times during a period of time when the specimen moves through an area irradiated by the irradiation spot.

7. The method according to claim 1, wherein the substantially circular irradiation spot is larger than a size of the specimen.

8. The method according to claim 1, wherein the position information includes directional vectors of the specimen.

9. The method according to claim 1, wherein the scanning using the second light source is performed under a condition satisfying the following Expression (2):

$$\frac{D_4}{v_1} > \frac{D_1}{v_3} \quad (2)$$

where $v_1$ is the speed of movement of the specimen in the interior of the flow channel, $v_3$ is the scanning speed of light for obtaining positional information, $D_1$ is the width of the flow channel, and $D_4$ is the diameter of the second irradiation spot.

10. The method according to claim 1, wherein different positions in the flow channel direction and the widthwise direction of the flow channel are irradiated with the second irradiation spot to obtain the positional information.

11. The method according to claim 1, wherein the positional information includes position information in the widthwise direction of the flow channel, in the flow channel direction, and a depth direction that is orthogonal to the widthwise and flow channel directions.

12. The method according to claim 1, further comprising:
obtaining positional information of the specimen subsequent to irradiating the specimen with the directional light by irradiating the specimen with light from a third light source.

13. The method according to claim 12, wherein obtaining positional information of the specimen subsequent to irradiating the specimen with the directional light includes:
irradiating the specimen by performing scanning with a third irradiation spot from the third light source, and
detecting a measurement light that is generated by the irradiation of the specimen by the third light source.

14. The method according to claim 13, wherein different positions in the flow channel direction and the widthwise direction of the flow channel are irradiated with the third irradiation spot to obtain the positional information.

* * * * *